(12) United States Patent
Chaudhari et al.

(10) Patent No.: US 6,660,675 B2
(45) Date of Patent: Dec. 9, 2003

(54) NOBLE METAL CONTAINING HYDROGENATION CATALYST FOR SELECTIVE HYDROGENATION OF 1, 4 BUTYNEDIOL TO 1, 4 BUTENEDIOL, AND A PROCESS FOR THE PREPARATION THEREOF

(75) Inventors: Raghunath Vitthal Chaudhari, Pune (IN); Chandrashekhar Vasant Rode, Pune (IN); Rengaswamy Jaganathan, Pune (IN); Manisha Madhukar Telkar, Pune (IN); Vilas Hari Rane, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 148 days.

(21) Appl. No.: 09/941,502

(22) Filed: Aug. 28, 2001

(65) Prior Publication Data

US 2002/0099244 A1 Jul. 25, 2002

Related U.S. Application Data

(62) Division of application No. 09/716,706, filed on Nov. 20, 2000.

(51) Int. Cl.[7] .......................... B01J 23/44; B01J 27/232; B01J 29/68
(52) U.S. Cl. ............................. 502/66; 502/71; 502/74; 502/77; 502/326; 502/328; 502/337; 502/339; 502/340
(58) Field of Search ................................. 502/104, 107, 502/328, 325, 326, 337, 339, 340, 64, 66, 74, 71, 77; 582/514

(56) References Cited

U.S. PATENT DOCUMENTS

| | | | | |
|---|---|---|---|---|
| 4,212,854 A | * | 7/1980 | Maki et al. ................... | 423/247 |
| 4,257,872 A | * | 3/1981 | La Pierre et al. .............. | 208/59 |
| 4,401,830 A | * | 8/1983 | Umumura et al. ........... | 562/478 |
| 4,692,534 A | * | 9/1987 | Bertholet ..................... | 549/456 |
| 5,063,194 A | * | 11/1991 | Broecker et al. ............ | 502/314 |
| 5,689,027 A | * | 11/1997 | Abichandani et al. ....... | 585/481 |
| 5,892,102 A | * | 4/1999 | Mikami et al. .............. | 560/210 |
| 5,942,645 A | * | 8/1999 | Rutter et al. ................. | 568/832 |
| 6,080,377 A | * | 6/2000 | Deeba et al. ............. | 423/239.2 |
| 6,265,343 B1 | * | 7/2001 | Daly et al. .................... | 502/339 |
| 6,420,615 B1 | * | 7/2002 | Chaudhari et al. ........... | 568/857 |
| 6,469,221 B1 | * | 10/2002 | Chaudhari et al. ........... | 568/861 |
| 6,528,689 B2 | * | 3/2003 | Chaudhari et al. ........... | 568/861 |

OTHER PUBLICATIONS

Fukada, Tosao, Bul. Chem. Soc. Japan (1958), 31, pp. 343–347.*

* cited by examiner

*Primary Examiner*—Tom Dunn
*Assistant Examiner*—Christina Ildebrando
(74) *Attorney, Agent, or Firm*—Ladas & Parry

(57) ABSTRACT

A hydrogenation catalyst of the general formula AB(y)C(z) wherein A is a support comprising of a salt of a Group II A metal or zeolite, B is a noble metal selected from Pt or Pd, y=0.2 to 10%, C is nickel and z=0 to 15.0%, with the proviso that when B is Pt, z=0.

7 Claims, No Drawings

NOBLE METAL CONTAINING HYDROGENATION CATALYST FOR SELECTIVE HYDROGENATION OF 1, 4 BUTYNEDIOL TO 1, 4 BUTENEDIOL, AND A PROCESS FOR THE PREPARATION THEREOF

This application is a divisional of copending application Ser. No. 09/716,706, filed Nov. 20, 2000, now pending.

FIELD OF THE INVENTION

The present invention relates to a noble metal containing hydrogenation catalyst for the selective hydrogenation of 1,4 butynediol to 1,4 butenediol. The present invention also relates to a process for the preparation of the said catalyst. More particularly, the present invention relates to said hydrogenation catalyst for the selective preparation of 1,4 butynediol to 1,4 butenediol, and a process for the preparation of the said catalyst.

BACKGROUND OF THE INVENTION 1,4 butenediol is a useful intermediate in the production of pesticide, insecticide and vitamin $B_6$. Being an unsaturated diol it can be used in the synthesis of many organic products such as tetrahydrofuran, n-methyl pyrrolidione, γ-butyrolactone, etc. It is also used as an additive in the paper industry, as a stabiliser in resin manufacture, as a lubricant for bearing systems and in the synthesis of allyl phosphates.

Prior art discloses the use of a number of catalysts for the manufacture of 1,4 butenediol by the hydrogenation of 1,4 butynediol. Most of the prior art patents are based on a combination of palladium with one or more mixed compounds of copper, zinc, calcium, cadmium, lead, alumna, mercury, tellurium, gallium, etc. GB A 871804 describes the selective hydrogenation of acetylinic compound in a suspension method using a Pd catalyst which has been treated with the salt solutions of Zn, Cd, Hg, Ga, Th, In, or Ga. The process is carried out at milder conditions with 97% selectivity for cis 1,2-butenediol and 3% to the transform. Moreover, use of organic amines have been suggested as promoters in the catalyst system.

U.S. Pat. No. 2,681,938 discloses the use of a Lindlar catalyst (lead doped Pd catalyst), for the selective hydrogenation of acetylinic compounds. The drawback of this process is the use of additional amines such as pyridine to obtain good selectivity for 1,4 butenediol.

German patent DE 1, 213, 839 describes a Pd catalyst doped with Zn salts and ammonia for the partial hydrogenation of acetylinic compounds. However, this catalyst suffers from the drawback of short lifetime due to poisoning.

German patent application DE A 2, 619, 660 describes the use of $Pd/Al_2O_3$ catalyst that has been treated with carbon monoxide for the hydrogenation of butynediol in an inert solvent. The disadvantage of this catalyst is that is treated with carbon monoxide gas which is highly toxic and difficult to handle.

U.S. Pat. No. 2,961,471 discloses a Raney nickel catalyst useful for the partial hydrogenation of 1,4 butynediol. The catalyst of this process gives a low selectivity for 1,4 butenediol. Another U.S. Pat. No. 2,953,604 describes a Pd containing charcoal and copper catalyst for the reduction of 1,4 butynediol to 1,4 butenediol with 81% selectivity for 1,4 butenediol. However, this process results in the formation of a large number of side products and is therefore undesirable.

U.S. Pat. No. 4,001,344 discloses the use of palladium mixed with γ-$Al_2O_3$ along with both zinc and cadmium or either zinc or cadmium together with bismuth or tellurium for the preparation of 1,4 butenediol by the selective hydrogenation of 1,4 butynediol. However, a large number of residues are formed (7.5–12%) which lowers the selectivity of 1,4 butenediol to 88%.

U.S. Pat. Nos. 5,521,139 and 5,278,900 describes the use of a Pd containing catalyst for the hydrogenation of 1,4 butynediol to prepare 1,4 butenediol. The catalyst used is a fixed bed catalyst prepared by applying Pd and Pb or Pd and Cd successively by vapor deposition or sputtering to a metal gauze or a metal foil acting as a support. In this process also the selectivity obtained for cis 1,4 butenediol is 98%. The disadvantage of this process is that a trans butenediol with residues are also obtained.

All the above catalysts for the hydrogenation of butynediol to butenediol suffer from disadvantages such as they contain more than two metals along with other promoters such as organic amines. Their preparation becomes cumbersome and all the reported catalysts do not give complete selectivity for the desired product 1,4 butenediol. The formation of side products and residues have also been reported which affect the efficiency of the process and the recovery of pure 1,4 butenediol is difficult. Another disadvantage that prior art catalysts suffer from is short life due to fast deactivation.

It is therefore important to obtain and/or develop catalysts that overcome the disadvantages of prior art catalysts used in the hydrogenation of 1,4 butynediol to 1,4 butenediol enumerated above.

OBJECTS OF THE INVENTION

The main object of the invention is to provide a novel hydrogenation catalyst for the selective preparation of 1,4 butenediol that comprises a noble metal, individually or in combination with nickel, on a suitable support without poisoning at very specific preparation conditions for the selective production of 1,4 butenediol.

It is another object of the invention to provide a process for the preparation of such novel hydrogenation catalysts for the preparation of 1,4 butenediol.

It is another object of the invention to provide a novel hydrogenation catalyst for the preparation of 1,4 butenediol that results in 100% conversion of the butynediol and 100% selectivity at mild process conditions.

It is another object of the invention to provide a catalyst with high stability that can be recycled several times without loss of activity and selectivity.

It is another object of the invention to provide a process for the preparation of 1,4 butenediol using the hydrogenation catalyst of the invention.

It is another object of the invention is to provide a novel catalyst for the selective hydrogenation of 1,4 butynediol to 1,4 butenediol that comprises only platinum on a suitable support, without poisoning at very specific preparation conditions.

It is an object of the invention to provide a process for the preparation of 1,4 butenediol from 1,4 butynediol using a novel hydrogenation catalyst resulting in 1,4 butenediol of high purity by mere separation of the catalyst.

SUMMARY OF THE INVENTION

Accordingly the present invention provides a hydrogenation catalyst of the general formula AB(y)C(z) wherein A is a support comprising of a salt of a Group II A metal or zeolite, B is a noble metal selected from palladium and platinum, y=0.2 to 10%, C is nickel and z=0 to 15.0% with the proviso that when B is Pt, z=0.

In one embodiment of the invention, B is Pd and z=0.2–10%.

The present invention also relates to a process for the preparation of a hydrogenation catalyst of the general formula AB(y)C(z) wherein A is a support comprising of a salt of a Group II A metal or zeolite, B is a noble metal selected from palladium and platinum, y=0.2 to 10%, C is nickel and z=0 to 15.0% with the proviso that when B is Pt, z=0, said process comprising:

i. dissolving a noble metal precursor in a mineral acid by stirring at a temperature in the range between 60° C. to 120° C.;
ii. diluting the above solution by adding water;
iii. adjusting the pH of the solution to the range of 8–12 by adding a base;
iv. adding a support to the above solution;
v. heating the mixture to a temperature in the range of 60° C. to 120° C.;
vi. reducing the above mixture using a conventional reducing agent;
vii. separating the catalyst formed by any conventional method;
viii. washing and drying the product to obtain the said catalyst.

In a further embodiment of the invention, the noble metal comprises of palladium and z=0.2 to 15%, the catalyst obtained at the end of step viii above is mixed with a solution of nickel in a basic medium having a pH in the range of 8–12, the mixture stirred for about 1 hour and the catalyst is separated by any conventional method. The catalyst is then dried at about 150° C. up to 10 hours in static air, reduced at a temperature in the range of between 390–420° C. for a time period in the range of between 5–12 hours in a flow of hydrogen, the reduced catalyst is then separated by any conventional method and washed and dried to obtain the final catalyst containing palladium and nickel.

In one embodiment of the invention, the noble metal source is a noble metal salt selected from the group consisting of acetate, bromide, and chloride and the source of nickel is a salt of nickel selected from the group consisting of acetate, carbonate, chloride and nitrate.

In another embodiment of the invention, the support is a Group II A metal salt selected from the group consisting of acetates, nitrates, chlorides and carbonates of magnesium, calcium and barium and the source of zeolite is $NH_4$-ZSM5.

In a further embodiment of the invention, the base used may be selected from the group consisting of sodium carbonate, potassium carbonate, potassium hydroxide, and sodium hydroxide.

In another embodiment of the invention, the reducing agent used is selected from the group consisting of hydrazine hydrate, hydrogen containing gas, and formaldehyde.

The present invention also relates to a process for the preparation of 1,4 butenediol from 1,4 butynediol said process comprising subjecting the 1,4 butynediol to hydrogenation by any conventional method characterised in that the catalyst used for the hydrogenation is of the general formula AB(y)C(z) wherein A is a support comprising of a salt of a Group II A metal or zeolite, B is a noble metal selected from palladium and platinum, y=0.2 to 10%, C is nickel and z=0 to 15.0%.

In a further embodiment of the invention, the selectivity of the process at milder process conditions is 100%

The present invention also relates to the use of a novel hydrogenation catalyst of the general formula AB(y)C(z) wherein A is a support comprising of a salt of a Group II A metal or zeolite, B is a noble metal, y=0.2 to 10%, C is nickel and z=0 to 15.0%, for the preparation of 1,4 butenediol.

DETAILED DESCRIPTION OF THE INVENTION

The present invention achieves 100% conversion of 1,4 butynediol with 100% selectivity for cis 1,4 butenediol at mild process conditions. At higher temperatures, while 1,4 butynediol is converted completely, the selectivity for cis 1,4 butenediol is less, generally <90%. The formation of side products such as acetals, γ-hydroxybutaraldehyde, butanol at higher temperatures is also more pronounced.

The hydrogenation of 1,4 butynediol to 1,4 butenediol is carried out in an autoclave under stirring conditions in the presence of Pd or Pt containing catalyst suspended in a mixture of 1,4 butynediol in water at 50° C. and 350 psig of $H_2$ pressure. The mixture is made alkaline (pH=8–10) by the addition of ammonia. Before pressurising the autoclave, it was ensured that there was no air in the autoclave. The hydrogenation is complete when the absorption of hydrogen is stopped or unchanged. After the reaction was complete, the reactor was cooled below ambient temperature and the contents were discharged and the reaction mixture analysed using a gas chromatography.

The catalyst prepared as per the procedure described below in the examples can be reduced in a muffle furnace at 400° C. in hydrogen flow for a time period ranging between 5–12 hours, preferably 7 hours.

In a feature of the invention, high purity 1,4 butenediol can be simply obtained by the removal of the catalyst from the product stream.

The present invention is described below by way of examples. However, the following examples are illustrative and should not be construed as limiting the scope of the invention.

EXAMPLE 1

Preparation of 1% Pd/$MgCO_3$ Catalyst 0.17 gms of palladium chloride was dissolved in 4 ml of hydrochloric acid and stirred at 80° C. till the palladium chloride was completely dissolved. The resultant solution was diluted by adding 50 ml of water and stirring for 2 hours, the pH being maintained between 9–10 by the addition of sodium hydroxide. To the diluted solution, 10.02 gms of magnesium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 2

Preparation of 1% Pd/$CaCO_3$ Catalyst 0.17 gms of palladium chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.12 gms of calcium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 3

Recycling of 1% Pd/CaCO₃ Catalyst

This example illustrates the recycling of 1% Pd/CaCO3 catalyst wherein the catalyst preparation was similar to the disclosure in Example 2 above. The hydrogenation of 1,4 butynediol was carried out by recycling the catalyst 10 times at 50° C. and 350 psig $H_2$ pressure as described earlier.

EXAMPLE 4

Preparation of 1% Pd/BaCO₃ Catalyst 0.16 gms of palladium chloride was dissolved in 4 ml of hydrochloric acid and stirred at 80° C. till the palladium chloride was completely dissolved. The resultant solution was diluted by adding 50 ml of water and stirring for 2 hours, the pH being maintained between 9–10 by the addition of sodium hydroxide. To the diluted solution, 10.1 gms of barium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 5

Preparation of 1% Pd/NH₄-ZSM5 Catalyst 0.17 gms of palladium chloride was dissolved in 4 ml of hydrochloric acid and stirred at 80° C. till the palladium chloride was completely dissolved. The resultant solution was diluted by adding 50 ml of water and stirring for 2 hours, the pH being maintained between 9–10 by the addition of sodium hydroxide. To the diluted solution, 10.0 gms of NH₄-ZSM5 was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 6

Preparation of 10% Ni— 1% Pd/CaCO₃ Catalyst 0.17 gms of palladium chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.12 gms of calcium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours. The dried catalyst is then mixed with a solution of nickel nitrate and stirred in basic medium (pH=9–10) for 1 hour, dried at 150° C. for 10 hours in static air and then reduced at 400° C. for 7 hours in a flow of hydrogen.

EXAMPLE 7

Preparation of 1% Pt/MgCO₃ Catalyst 0.16 gms of platinum chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.13 gms of magnesium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 8

Preparation of 1% Pt/CaCO₃ Catalyst 0.17 gms of platinum chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.03 gms of calcium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 9

Preparation of 1% Pt/BaCO₃ Catalyst 0.16 gms of platinum chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.05 gms of barium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 10

Performance of Palladium or Palladium and Nickel Supported Catalysts of the Invention as Prepared in Examples 1–6 Above This example illustrates the performance of the palladium or palladium and nickel supported catalysts of the invention as prepared in Examples 1–6 above in the hydrogenation of 1,4 butynediol to 1,4 butenediol.

| Example No. | Catalyst | Conversion of 1, 4 butynediol (%) | Selectivity to cis 1, 4 butenediol (%) | Reaction period (hours) |
|---|---|---|---|---|
| 1 | 1% Pd/MgCO₃ | 100 | 99.8 | 2 |
| 2 | 1% Pd/CaCO₃ | 100 | 98.2 | 1 |
| 3 | 1% Pd/CaCO₃* | 100 | 98 | 68 |
| 4 | 1% Pd/BaCO₃ | 100 | 100 | 2 |
| 5 | 1% Pd/NH₄-ZSM 5 | 100 | 100 | 4 |
| 6 | 10% Ni- 1% Pd/CaCO₃ | 100 | 100 | 4 |

*catalyst recycled for 10 times

EXAMPLE 11

Performance of Platinum Supported Catalysts of the Invention as Compared in Examples 7–9 Above This example illustrates the performance of the platinum supported catalysts of the invention as prepared in Examples 7–9 above in the hydrogenation of 1,4 butynediol to 1,4 butenediol.

| Example No. | Catalyst | Conversion of 1, 4 butynediol (%) | Selectivity to cis 1,4 butenediol (%) | Reaction period hours |
|---|---|---|---|---|
| 7 | 1% Pt/MgCO$_3$ | 100 | 99.8 | 2 |
| 8 | 1% Pt/CaCO$_3$ | 100 | 100 | 1 |
| 9 | 1% Pt/BaCO$_3$ | 100 | 99.9 | 2.5 |

ADVANTAGES OF THE INVENTION

1. The catalyst of the invention is useful for the selective hydrogenation of 1,4 butynediol to 1,4 butendiol without poisoning.
2. Substantially complete conversion of 1,4 butynediol to 1,4 butenediol with almost 100% selectivity to cis 1,4 butenediol is obtained at milder process conditions.
3. The separation of the product 1,4 butenediol in pure form is achieved easily by the removal of the catalyst from the reaction mixture.
4. The catalyst of the invention is capable of recycling several times without loss of activity or selectivity. The turn over number also is good.

We claim:

1. A process for the preparation of a hydrogenation catalyst of the general formula AB(y)C(z) wherein A is a support comprising of a salt of a Group II A metal or zeolite, B is a noble metal selected from Pd or Pt, y=0.2 to 10%, C is nickel and z=0 to 15.0%, with the proviso that when B is Pt, z=0, said process comprising:
   i. dissolving a noble metal precursor in a mineral acid by stirring at a temperature in the range between 60° C. to 120° C.;
   ii. diluting the above solution by adding water;
   iii. adjusting the pH of the solution to the range of 8–12 by adding a base;
   iv. adding a support to the above solution;
   v. heating the mixture to a temperature in the range of 60° C. to 120° C.;
   vi. reducing the above mixture using a conventional reducing agent;
   vii. separating the catalyst formed by any conventional method;
   viii. washing and drying the product to obtain the catalyst.

2. A process as claimed in claim 1 wherein the catalyst obtained at the end of step viii is mixed with a solution of nickel in a basic medium having a pH in the range of 8–12; stirred for about 1 hour; the catalyst formed is separated by any conventional method; dried at about 150° C. up to 10 hours in static air; reduced at a temperature in the range of between 390–420° C. for a time period in the range of between 5–12 hours in a flow of hydrogen; the product being separated, washed and dried to obtain the catalyst.

3. A process as claimed in claim 1 wherein the noble metal source is a salt of a noble metal selected from the group consisting of acetate, bromide, and chloride of and the source of nickel is a salt of nickel selected from the group consisting of acetate, carbonate, chloride and nitrate.

4. A process as claimed in claim 1 wherein the support is a salt of a Group II A metal selected from the group consisting of acetates, nitrates, chlorides and carbonates of magnesium, calcium and barium and the source of zeolite is NH$_4$-ZSM5.

5. A process as claimed in claim 1 wherein the base used is selected from the group consisting of sodium carbonate, potassium carbonate, potassium hydroxide, and sodium hydroxide.

6. A process as claimed in claim 1 wherein the reducing agent used is selected from the group consisting of hydrazine hydrate, hydrogen containing gas, and formaldehyde.

7. A process as claimed in claim 1 wherein A is a support comprising of a salt of a Group II A metal, B is platinum and y=0.2 to 10%, said process comprising:
   i. dissolving a platinum precursor in a mineral acid by stirring at a temperature in the range between 60° C. to 120° C.;
   ii. diluting the above solution by adding water;
   iii. adjusting the pH of the solution to the range of 8–12 by adding a base;
   iv. adding a support to the above solution;
   v. heating the mixture to a temperature in the range of 60° C. to 120° C.;
   vi. reducing the above mixture using a conventional reducing agent;
   vii. separating the catalyst formed by any conventional method;
   viii. washing and drying the product to obtain the desired catalyst.

* * * * *